United States Patent
Frawley et al.

(10) Patent No.: US 7,419,831 B2
(45) Date of Patent: Sep. 2, 2008

(54) METHOD AND APPARATUS FOR DETERMINATION OF WATER AND FOR NORMAL PHASE LIQUID CHROMATOGRAPHY

(75) Inventors: Nile Nelson Frawley, Midland, MI (US); Jeffrey Robert Larson, Midland, MI (US); Mark William Beach, Midland, MI (US); Mark Lindsay Dittenhafer, Midland, MI (US); Steven Randall Erskine, Lake Jackson, TX (US); Joseph J. Kiefer, Auburn, MI (US)

(73) Assignee: Dow Global Technologies, Inc., Midland, MI (US)

( * ) Notice: Subject to any disclaimer, the term of this patent is extended or adjusted under 35 U.S.C. 154(b) by 885 days.

(21) Appl. No.: 10/487,103

(22) PCT Filed: Aug. 20, 2002

(86) PCT No.: PCT/US02/26658

§ 371 (c)(1), (2), (4) Date: Feb. 17, 2004

(87) PCT Pub. No.: WO03/019176

PCT Pub. Date: Mar. 6, 2003

(65) Prior Publication Data

US 2004/0241863 A1 Dec. 2, 2004

Related U.S. Application Data

(60) Provisional application No. 60/314,036, filed on Aug. 22, 2001.

(51) Int. Cl.
*G01N 33/18* (2006.01)

(52) U.S. Cl. .............................. 436/39; 436/8; 436/42; 436/161; 436/174; 436/175; 436/177; 436/178; 422/68.1; 422/69; 422/89; 422/101; 210/656

(58) Field of Classification Search ................ 436/8, 436/39, 42, 161, 174, 175, 177, 178, 181; 422/68.1, 69, 70, 101, 89; 210/656, 150, 210/151
See application file for complete search history.

(56) References Cited

U.S. PATENT DOCUMENTS 4,846,977 A * 7/1989 DeVellis et al. ............. 210/640

(Continued)

FOREIGN PATENT DOCUMENTS

EP 0816843 1/1998

OTHER PUBLICATIONS

Jalbert, J. et al. Analytical Chemistry, vol. 71, No. 15, Aug. 1, 1999, pp. 3283-3291.*

(Continued)

*Primary Examiner*—Maureen M Wallenhorst

(57) ABSTRACT

A method for calibrating an analysis instrument, e.g., a gas chromatograph, for water analysis that includes four steps. The first step is to continuously remove water from a liquid that contains water to produce a liquid containing a reduced amount of water such as by membrane pervaporation. The second step is to analyze the liquid containing a reduced amount of water for water by a reference water analysis method such as by Karl Fischer titration. The third step is to analyze the stream of liquid containing a reduced amount of water using the instrument to be calibrated, e.g., a gas chromatograph having a helium photoionization pulse discharge detector. The fourth step is to calibrate the instrument using the analysis of the second step. In a related embodiment, a system for normal phase chromatography.

63 Claims, 7 Drawing Sheets

U.S. PATENT DOCUMENTS

| | | | |
|---|---|---|---|
| 4,846,997 A | | 7/1989 | Sandkuehler et al. |
| 5,340,541 A | * | 8/1994 | Jackson et al. ............... 422/75 |
| 5,433,861 A | | 7/1995 | Frawley et al. |
| 5,442,968 A | * | 8/1995 | Westlake et al. ......... 73/863.23 |
| 5,469,917 A | | 11/1995 | Wolcott |

OTHER PUBLICATIONS

Ewen, John et al., "Syndiospecific Propylene Polymerizations with Group 4 Metallocenes", Journal of the American Chemical Society, vol. 110, pp. 6255-6256 (1988).

Gilbert, Roland et al., "Bias Assessment of Current Technologies Used for the Determination of Low Levels of Moisture in Mineral Oil Samples", Analytical Chemistry, vol. 73, pp. 520-526 (Feb. 1, 2001).

Heftmann, E., "Fundamentals and Applications of Chromatographic and Electrophoretic Methods", Journal of Chromatography/Library, vol. 22A, pp. A75-A78 (1983).

Herberich, Gerhard E. et al., "Borabenzene Derivatives. 22.[1] Synthesis of Boratabenzene Salts from 2,4-Pentadienylboranes. Structure of [NMe3Ph][C5H5BMe]", Organometallics, vol. 14, No. 1, pp. 471-480 (1995).

Jalbert, J. et al., "Simultaneous Determination of Dissolved Gases and Moisture in Mineral Insulating Oils by Static Headspace Gas Chromatography with Helium Photoionization Pulsed Discharge Detection", Analytical Chemistry, vol. 73, pp. 3382-3391 Jul. 15, 2001).

Stetter, J.R. et al., "New Sensor Arrays and Sampling Systems for a Modular Electronic Nose", Sensors and Actuators B, vol. 69, pp. 410-419 (2000).

Van de Merbel, N.C., "Membrane-Based Sample Preparation Coupled On-Line to Chromatography or Electrophoresis", Journal of Chromatography A, vol. 856, pp. 55-82 (1999).

Wentworth, W.E. et al., "Pulsed Discharge Helium Ionization Detector", Chromatographia, vol. 34, No. 5-8., pp. 219-225 (Sep./Oct. 1992).

Wild, Ferdinand et al., "Synthesis and Molecular Structures of Chiral *ansa*-Titanocene Derivatives with Bridged Tetrahydroindenyl Ligands", Journal of Organometallic Chemistry, vol. 232, pp. 233-247 (1982).

* cited by examiner

METHOD AND APPARATUS FOR DETERMINATION OF WATER AND FOR NORMAL PHASE LIQUID CHROMATOGRAPHY

This application claims priority to U.S. Provisional Application Ser. No. 60/314,036 filed Aug. 22, 2001 and to PCT Application Ser. No. PCT/US02/26658 filed Aug. 22, 2002.

BACKGROUND

Aquametry or the determination of water in a material is an important branch of chemical analysis. The most common chemical analysis method for the determination of water is the Karl Fischer titration. However, other chemical analysis methods, such as Gas Chromatography (GC), are also widely used; see Gilbert et al., Anal. Chem., 2001, p520-526.

When most chemical analysis instruments are used to determine water in a liquid, the instrument must be calibrated by analyzing a liquid "standard" having a known water concentration. Calibrating a chemical analysis instrument for the determination of water at relatively low concentrations (e.g., in the range of 1 part per million) is difficult because it is difficult to prepare a liquid standard having such a relatively low water concentration because water from the environment tends to contaminate the liquid standard.

Normal phase liquid chromatography (NPLC) is an important chemical analysis technique, see Heftmann, Journal of Chromatography Library, Volume 22A, pages A75-A78. However, the water concentration of the relatively non-polar mobile phase used in NPLC has a significant effect on the relative elution rate of the separated components of interest. Therefore, the mobile phase used in NPLC is usually kept as free of water as possible and/or a relatively polar "modulator", such as an alcohol is added to the mobile phase.

BRIEF SUMMARY OF THE INVENTION

The instant invention is a solution to the above-mentioned problems. The method and apparatus of the instant invention provide a system for drying and standardizing a liquid that is then used to calibrate an analysis instrument and provide for a NPLC system using a relatively dry mobile phase or a mobile phase containing water as a modulator.

More specifically, the instant invention is a method for calibrating an analysis instrument for water analysis, comprising the steps of: (a) continuously removing water from a liquid that contains water to produce a liquid containing a reduced amount of water; (b) analyzing the liquid containing a reduced amount of water for water using a reference water analysis method; (c) analyzing the liquid containing a reduced amount of water using the instrument to be calibrated; and (d) calibrating the analysis instrument using the analysis of step (b).

In another embodiment, the instant invention is a method for calibrating an analysis instrument for the determination of water, comprising the steps of: (a) diffusing water from a fluid having a controlled concentration of water through a membrane into a liquid to produce a liquid containing a controlled amount of water; (b) analyzing the liquid containing a controlled amount of water for water using a reference water analysis method; (c) analyzing the liquid containing a controlled amount of water using the instrument to be calibrated; and (d) calibrating the chemical analysis instrument using the analysis of step (b).

In another embodiment, the instant invention is an apparatus for calibrating an analysis instrument for the determination of water, comprising: (a) a liquid reservoir for containing a liquid, the liquid containing water; (b) a pump in liquid communication with the liquid reservoir for pumping a liquid contained in the reservoir; (c) a membrane dryer in liquid communication with the pump for pervaporation of water from a liquid pumped through the membrane dryer across a water permeable membrane into a stream of gas flowed through the membrane dryer or for diffusion of water from the stream of gas through the water permeable membrane into the liquid pumped through the membrane dryer; (d) a source of gas in fluid communication with the membrane dryer; and (e) a chemical analysis instrument in liquid communication with the membrane dryer for analyzing liquid from the membrane dryer.

In yet another embodiment, the instant invention is an improved normal phase liquid chromatography chemical analysis method comprising the step of flowing a non-polar mobile phase through a chromatography column containing a polar stationary phase, wherein the improvement comprises the step of: diffusing water from a controlled humidity fluid through a membrane into the mobile phase to produce a non-polar mobile phase containing a controlled amount of water prior to the step of flowing the mobile phase containing a controlled amount of water through the chromatography column.

In another embodiment, the instant invention is an improved normal phase liquid chromatography chemical analysis method comprising the step of flowing a non-polar mobile phase through a chromatography column containing a polar stationary phase, wherein the improvement comprises the step of: pervaporating water dispersed in the mobile phase through a membrane to produce a non-polar mobile phase containing a reduced amount of water prior to the step of flowing the mobile phase containing a reduced amount of water through the chromatography column.

In yet another embodiment, the instant invention is apparatus for normal phase liquid chromatography, comprising: a source of non-polar mobile phase; a membrane dryer in liquid communication with the source of non-polar mobile phase for pervaporation of water from a non-polar mobile phase flowed through the membrane dryer across a water permeable membrane into a stream of gas flowed through the membrane dryer or for diffusion of water from the stream of gas through the water permeable membrane into the non-polar mobile phase flowed through the membrane dryer; and a chromatography column containing a polar stationary phase in fluid communication with the membrane dryer.

In another embodiment, the instant invention is a method for the on-line analysis water in a chemical production process stream, in the concentration range of from 0.01 parts per million to 100 parts per million water, comprising the steps of: (a) contacting a liquid that contains water with one side of a membrane that is selectively more permeable to water than the liquid in order to produce a liquid containing a reduced amount of water; (b) analyzing the liquid containing a reduced amount of water for water by a reference water analysis method; (c) analyzing the liquid containing a reduced amount of water using the analysis instrument; (d) calibrating the analysis instrument using the determination of step (b); and (e) determining the water concentration of the process stream with the analysis instrument to determine the concentration of water in the process stream.

DETAILED DESCRIPTION OF THE INVENTION

Figure 1:
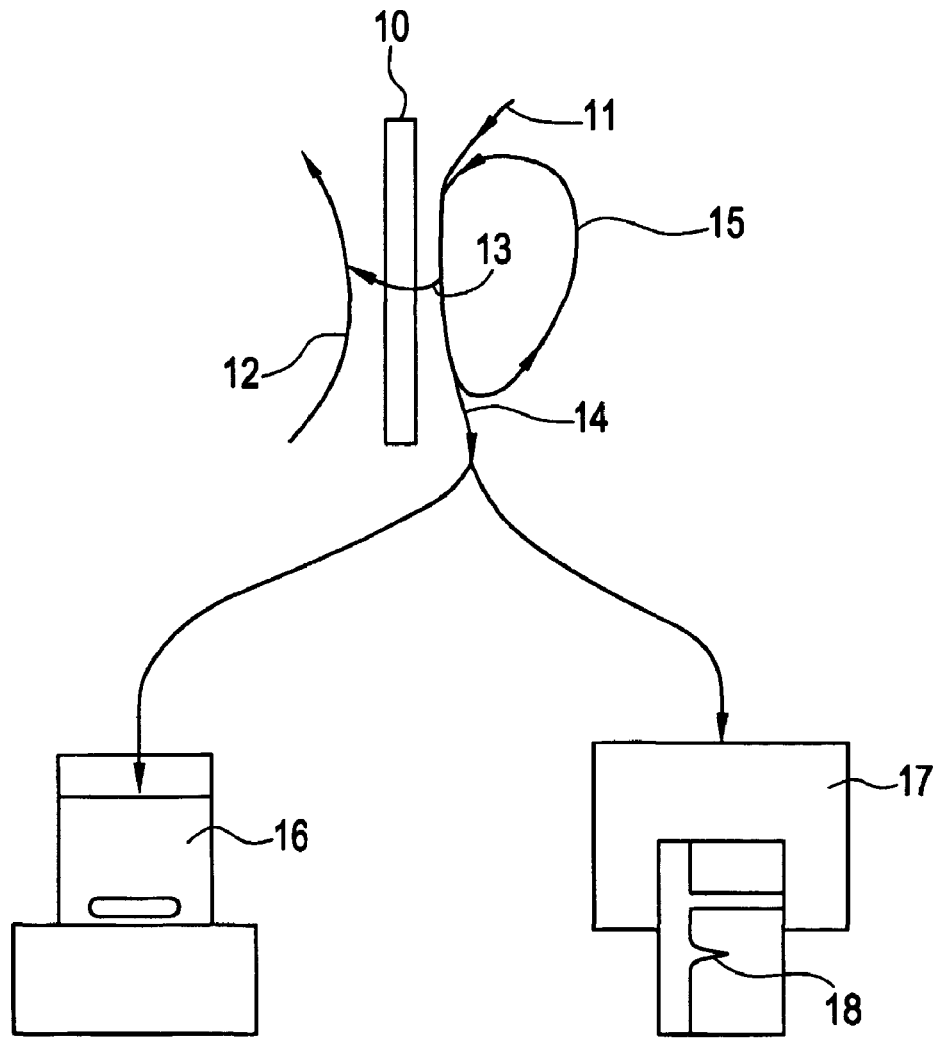
FIG. 1 is a schematic drawing showing the basic steps of a method embodiment of the instant invention.

Referring now to FIG. 1, therein is shown a schematic drawing depicting the basic steps of a method of the instant invention. A water permeable membrane 10 is used to partition a liquid containing water 11 from a gas 12 so that water 13 in the liquid 11 pervaporates from the liquid containing water 11, through the membrane 10 and into the gas 12 to produce a liquid containing a reduced amount of water 14. The liquid containing a reduced amount of water 14 can optionally be recycled 15 to further reduce the water concentration of the liquid containing a reduced amount of water 14.

Referring still to FIG. 1, the liquid containing water 11 is contacted with one side of the membrane 10 in order to pass at least a portion of the water 13 of the liquid through the membrane 10 to produce a liquid containing a reduced amount of water 14.

The water concentration of the liquid containing a reduced amount of water 14 is then analyzed using a reference water analysis method. For example, referring again to FIG. 1, the water concentration of the liquid containing a reduced amount of water 14 is analyzed using a coulometric Karl Fischer titration 16. However, it should be understood that the specific reference water analysis method used to analyze the water concentration of the liquid containing a reduced amount of water is not critical in the instant invention and can, for example, include, without limitation thereto, any of the methods described in Gilbert et al., Anal. Chem., 2001, p520-526, such as gas chromatography, gas-phase sensors or probes and liquid-phase sensors or probes.

Referring still to FIG. 1, the final step of the instant invention is to analyze the liquid containing a reduced amount of water 14 by, for example, Gas Chromatography or liquid chromatography, although gas chromatography is preferred, to produce a water response 18. Since the water concentration of the liquid containing a reduced amount of water 14 is known from the determination of the reference method, the gas chromatograph 17 can be calibrated by, for example, dividing the area or peak height of the response 18 by the concentration of water in the liquid containing a reduced amount of water 14.

The detector used in the gas chromatograph 17 can be any detector that responds to water such as a thermal conductivity detector or a helium photoionization pulse discharge detector (HPPDD). However, a HPPDD detector is most preferred in the instant invention. HPPDD detectors are commercially available from Valco Instruments and are described, for example, by Wentworth et al., Chromatographia, 34 (1992) p219-225.

Since the calibration curve of a chemical analysis instrument may not be linear and may not pass through the zero, zero origin, it is usually preferable to calibrate a chemical analysis instrument at several points within a range of water concentrations. Calibration at a very low water concentration can be accomplished in the instant invention, for example, by using the recycle feature of the instant invention. Calibration at a higher water concentration can be accomplished in the instant invention, for example, by using a single pass of the liquid through the membrane dryer. Calibration at a yet higher water concentration can be accomplished in the instant invention, for example, by using the technique described in the following paragraph.

Referring still to FIG. 1, if the gas 12, or other fluid, contains a controlled concentration of water, then water can diffuse through the membrane 10 in the reverse direction to that shown in FIG. 1 to produce a liquid 11 containing a controlled amount of water. This embodiment of the instant invention can be used to effectively prepare a calibration standard having a relatively higher concentration of water.

It should be understood that the pervaporation system shown in FIG. 1 is but one example of continuously removing water from a liquid that contains water to produce a liquid containing a reduced amount of water. For example, flowing the liquid through a bed of drying agent would be another example of continuously removing water from a liquid that contains water to produce a liquid containing a reduced amount of water.

Figure 2:
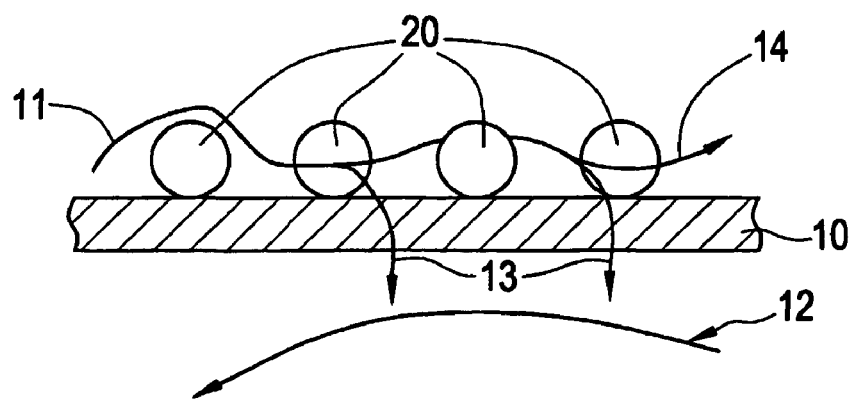
FIG. 2 is a side cross-sectional view of a pervaporation membrane of the instant invention that is partitioning a stream of liquid from a stream of gas, a static mixing element in the form of beads being placed adjacent the membrane in the stream of liquid.

Referring now to FIG. 2, therein is shown a side cross-sectional view of a pervaporation membrane 10 of the instant invention that is partitioning a stream of liquid containing water 11 from a gas. A static mixing element in the form of beads 20 positioned adjacent the membrane 10 in the stream of liquid containing water 11 mixes the stream of liquid containing water 11 so that the pervaporation of water 13 through the membrane 10 is more effective so that the concentration of water in the stream of liquid containing a reduced amount of water is lower than when the beads 20 are not used.

Referring still to FIG. 2, it should be understood that any desired means can be used to mix the liquid adjacent the membrane 10. The beads 20 are conveniently used when the membrane 10 is tubular in shape. When the membrane 10 is a sheet shaped membrane, then it may be preferable to use a screen or a fabric as a static mixing element.

Pervaporation of water from a liquid through a water permeable membrane into a gas stream is known, see, for example, U.S. Pat. No. 4,846,997 herein fully incorporated by reference. The use of a static mixer to improve the efficiency of pervaporation of water from a liquid through a water permeable membrane into a gas stream is also known, see, for example, U.S. Pat. No. 5,433,861 herein fully incorporated by reference. As disclosed in the '997 and '861 patents and in the instant invention, sulfonated halopolymers, such as DuPont NAFION brand perfluorosulfonic acid polymer, are preferred membrane materials for pervaporation of water from a liquid. Other membranes that can be used in the instant invention include other sulfonated polymers such as a sulfonated polyethylene membrane. However, it should be understood that any membrane could be used in the instant invention that is more permeable to water than the liquid. It should also be understood that the instant inventors intend that the claims of this application cover all such membranes now in existence or those that are developed in the future.

As mentioned above, at the present time membranes comprising NAFION brand perfluorosulfonic acid polymer are preferred in the instant invention. Membranes comprising NAFION brand perfluorosulfonic acid polymer are much more permeable to water than most any other liquid. For example, the ratio of the permeability of NAFION brand perfluorosulfonic acid polymer to water v. hexane is about one hundred million to one. For benzene, such ratio is about ten million to one. Hexane has a Polarity Index (P') of about 0.1 while benzene has a P' of about 2.7. Preferably, the P' of the liquid to be analyzed of the instant invention has a P' less than about 4. Liquids having a P' between about 4 and 5, such as ethyl acetate, are less preferred. Liquids having a P' greater than 5, such as methanol, are even less preferred.

Figure 3:
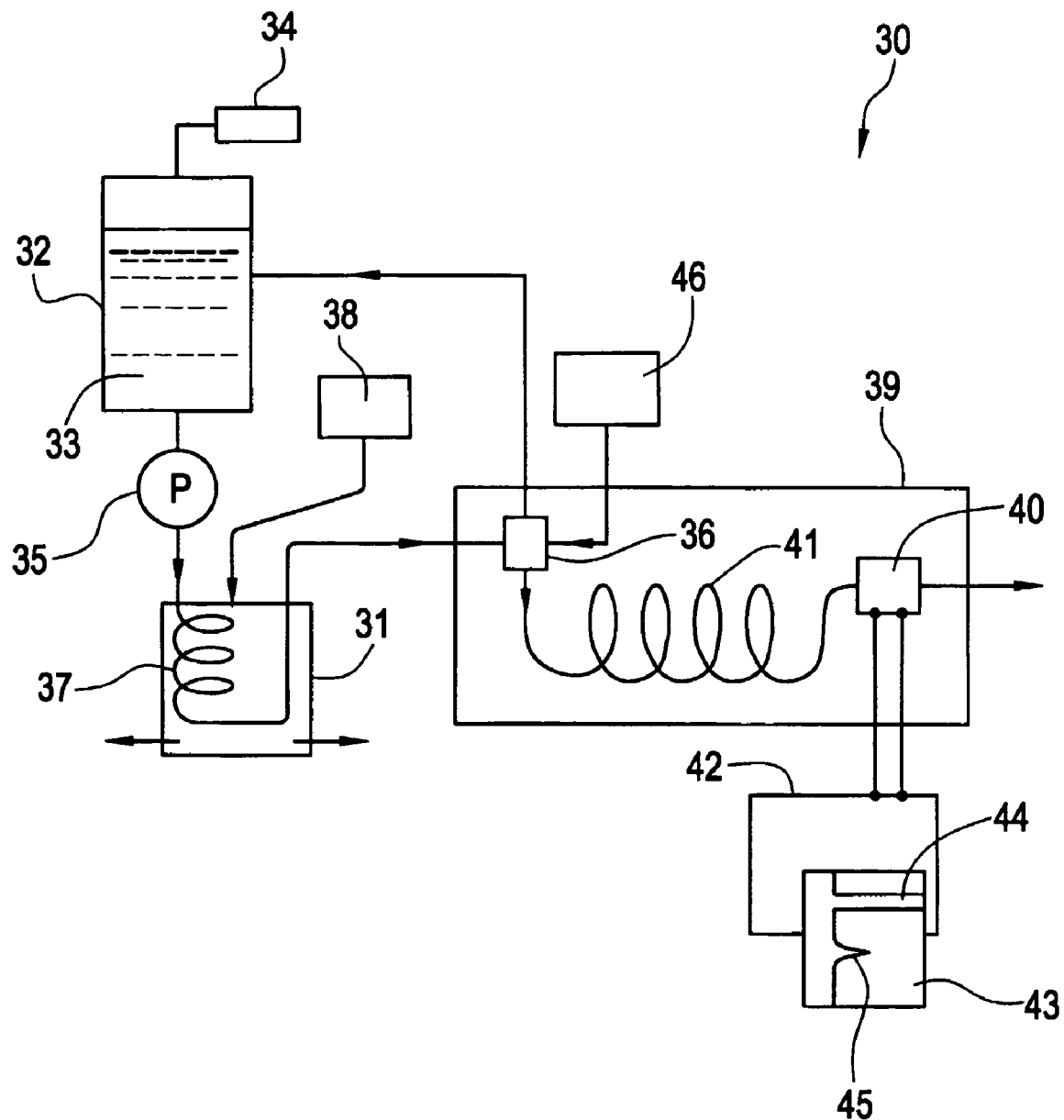
FIG. 3 is a schematic drawing of an apparatus embodiment of the instant invention, the apparatus including a membrane dryer for drying a liquid.
Figure 5:
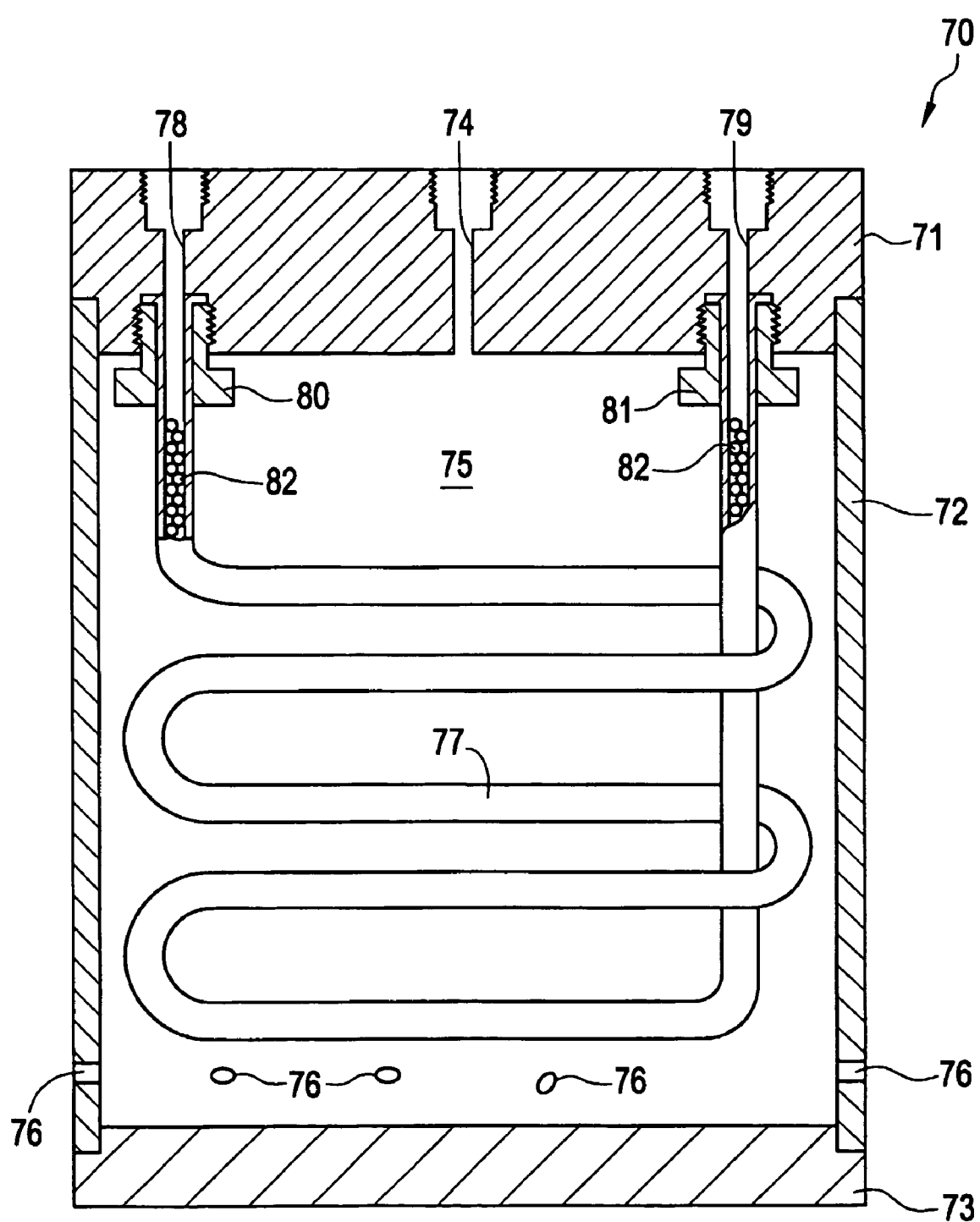
FIG. 5 is a side view, in full and in cross-section, of a preferred membrane dryer that can be used in the instant invention.

Referring now to FIG. 3, therein is shown a schematic drawing of an apparatus embodiment 30 of the instant invention, the apparatus 30 including a membrane dryer 31 for drying a liquid (the membrane dryer 31 is shown in greater detail in FIG. 5). The apparatus 30 includes a liquid reservoir 32 for containing a liquid 33, the liquid 33 containing water. A vent tube 34 filled with silica gel desiccant helps protect the liquid 33 from atmospheric moisture. A pump 35, such as a liquid chromatography eluant pump, is used to pump the liquid 33 through the membrane dryer 31, through a rotary injection valve 36 (such as a Valco Instruments Company 4-port 2-microliter rotary injection valve) and then back to the reservoir 32. The membrane dryer 31 is comprised of a tubular membrane 37 packed with glass beads. A source of gas 38 is used to flow gas around the outside of the tubular membrane 37.

Referring still to FIG. 3, the injection valve 36 is positioned in a gas chromatograph 39 (such as a Hewlett Packard Model 5890II gas chromatograph). A source of carrier gas 46 is also connected to the injection valve 36. The gas chromatograph 39 is equipped with a detector 40 that is capable of detecting water (such as a Valco Instruments Company model D-2-I helium photoionization pulse discharge detector). The detector 40 is in electrical communication with a computer 42 (such as a Spectra Physics 4400 Integrator) for producing a chromatogram 43.

A gas chromatography column 41 (such as a Restek Rtx-1701 capillary column, 60 meters long, 0.53 millimeters internal diameter, having a 3 micrometer thick stationary phase) is connected to the injection valve 36 and the detector 40 so that when the injection valve 36 is rotated from its load position to its inject position a 2 microliter injection of the liquid 33 is made into the column 41. The injected liquid 33 is chromatographed in the column 41 to produce the chromatogram 43. The chromatogram 43 shows a solvent peak 44 and a water peak 45.

The apparatus 30 can be calibrated by first determining the water concentration of the liquid 33 by a reference water analysis method such as a Karl Fischer titration and then dividing the peak area or peak height of the water peak 45 by the determined water concentration of the liquid 33. Such a calibration can be accurate over the linear response range of the detector 40.

When it is desired to obtain a calibration of the apparatus 30 at a relatively low water concentration, then it is best to recycle the liquid 33 for an extended time, e.g., for several hours, to reduce the water concentration of the liquid 33 to a relatively low level, e.g., to the low parts per million range. When such low levels are not desired, then it is not necessary to recycle the liquid 33 through the membrane dryer 31.

Ordinarily, the source of gas 38 is a gas having a very low water concentration, such as nitrogen gas from a high-pressure gas cylinder. However, if the source of gas 38 (or other fluid) has a higher water concentration, then, as discussed above in reference to FIG. 1, the water concentration of the liquid 33 flowed through the membrane dryer 31 will be higher and such a system can be used to obtain a calibration of the apparatus 30 at a higher water concentration. It should be understood that although not preferred, a stream of reduced pressure gas or even a vacuum source can be used as the source of gas 38.

Figure 4:
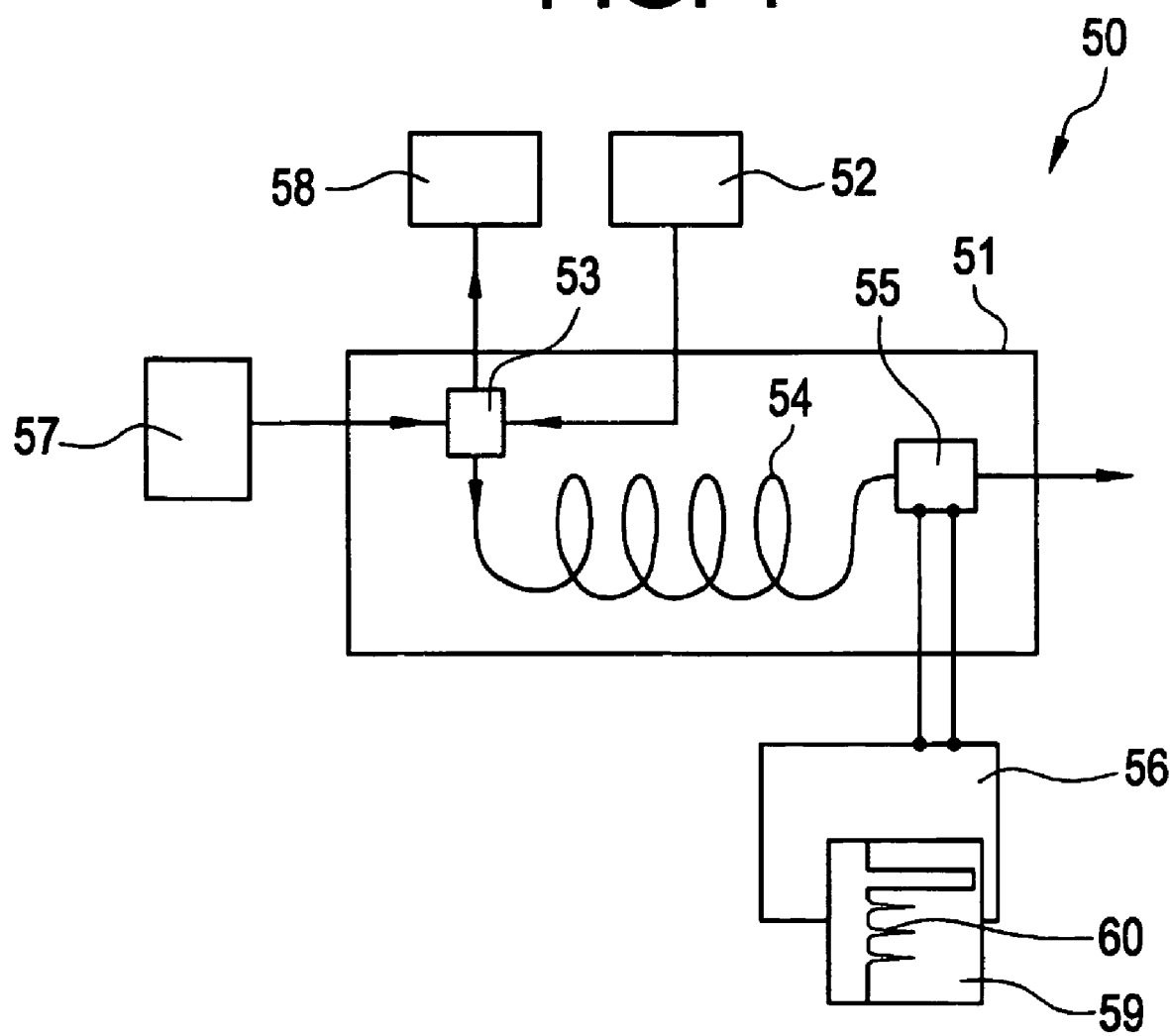
FIG. 4 is a schematic drawing of a system for the determination of water in a chemical production process.

Referring now to FIG. 4, therein is shown a schematic drawing of a Gas Chromatography system 50 for the determination of water in a chemical manufacture process stream. The system 50 includes a gas chromatograph 51 having a source of carrier gas 52, a rotary injection valve 53, a gas chromatography column 54, a detector 55 and a computer 56. The gas chromatograph 51 is the same gas chromatograph as gas chromatograph 39 of FIG. 3, except that the gas chromatograph 51 is now installed in a chemical manufacturing facility for the on-line determination of water in a process stream.

Referring still to FIG. 4, a source of the process stream 57 is flowed through the injection valve 53 to a waste vessel 58. When the injection valve 53 is rotated from its load to its inject position, a 2 microliter injection of the process stream 57 is made into the column 54. The process stream 57 is chromatographed in the column 54 to produce the chromatogram 59. The chromatogram 59 shows a water peak 60 that is measured by the computer 56. Since the apparatus 50 has been calibrated as described above, the computer 56 is able to determine and report the water concentration of the process stream 57.

Referring now to FIG. 5, therein is shown a side view, in full and in cross-section, of a preferred membrane dryer 70 that can be used in the instant invention. The membrane dryer 70 is constructed according to the teachings of U.S. Pat. No. 5,433,861. The membrane drier 70 has a clear plastic top 71, clear plastic cylindrical body 72, and clear plastic bottom 73. A sweep gas port 74 is provided in the top 71 so that a sweep gas can be flowed into the central cavity 75 of the membrane dryer 70. The sweep gas flows out of the cavity 75 by way of vents 76 in the body 72. A tubular membrane 77 (NAFION 815X brand perfluorosulfonic acid polymer membrane tubing from DuPont) is connected to an inlet port 78 in the top 71 using a plastic flange fitting 80 (available, for example, as part number P-501X from Chrom Tech, Inc., Apple Valley, Minn. 55124). The other end of the membrane 77 is connected to an outlet port 79 in the top 71 using a plastic flange fitting 81. The membrane 77 is filled with glass beads 82.

In the discussion above the chemical analysis instrument is a gas chromatograph. However, it should be understood that the chemical analysis instrument can be any chemical analysis instrument that is sensitive to water such as a spectroscopic instrument (e.g., infrared, near infrared, far infrared, conventional or Raman, or even a mass spectrometer) or a separations type instrument such as a liquid chromatograph or an electrophoresis based instrument such as a capillary electrophoresis instrument.

Referring again to FIG. 4, the process stream 57 can come from a process that comprises the step of polymerizing one or more olefins using a polymerization catalyst since the activity of such catalysts (or other catalysts) can be significantly influenced by water. On the other hand, the process stream 57 can come from a process wherein the thermal control of the process depends on controlling the water concentration of the process stream 57. However, it should be understood that the specific process stream is not critical in the instant invention.

When olefins are polymerized in the instant invention, preferably such olefins have from two to ten carbon atoms. Highly preferred olefins can be selected from the group consisting of ethylene, propylene, norborene, octane, styrene, butadiene and divinylbenzene.

Figure 8:
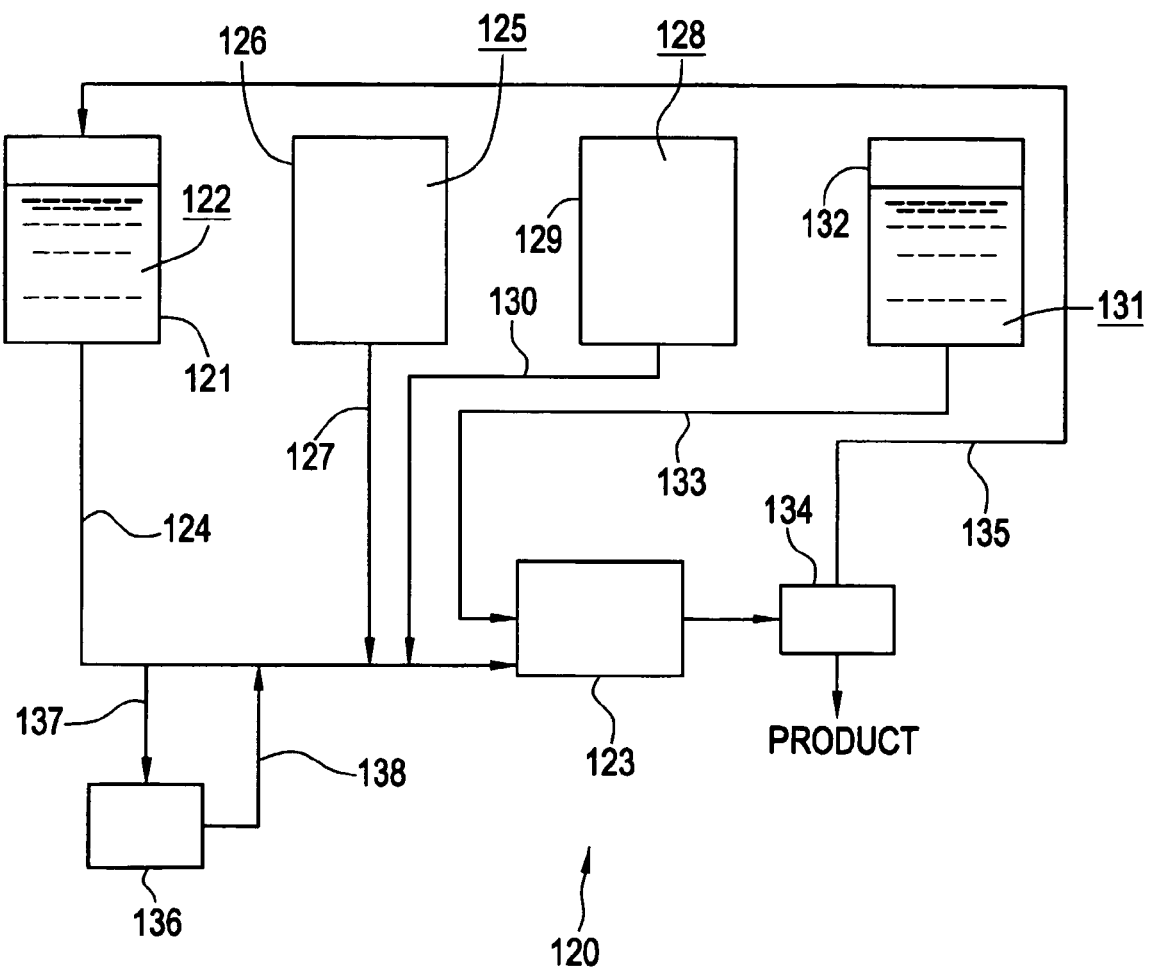
FIG. 8 is a schematic drawing of a chemical production process according to the instant invention for the polymerization of an olefin using a water sensitive polymerization catalyst.

Referring now to FIG. 8, therein is shown a schematic view of a chemical production process 120 for the production of polyethylene by the solution process. The process 120 includes a solvent tank 121 for containing octane 122. The octane 122 is pumped into a polymerization reactor 123 via a solvent pipe 124. Ethylene monomer 125 contained under pressure in ethylene monomer tank 126 is flowed into the stream of octane flowing into the reactor 123 via a monomer pipe 127. 1-octene co-monomer 128 contained under pressure in co-monomer tank 129 is flowed into the stream of octane flowing into the reactor 123 via a co-monomer pipe 130. Metallocene polymerization catalyst in octane 131 contained in catalyst tank 132 is flowed into the stream of octane flowing into the reactor 123 via a catalyst pipe 133.

The ethylene 125 and 1-octene 128 catalytically co-polymerize in the reactor 123 to form a solution of polyethylene/1-octene in octane that is then flowed to a separator 134. The separator 134 separates the octane from the polyethylene/1-octane product, the separated octane being recycled back to the solvent tank 121 via a recycle pipe 135. The ratio of ethylene to 1-octene in the polyethylene/1-octene co-polymer controls the density of the "polyethylene" product.

Metallocene polymerization catalysts are well known in the art and include derivatives of Group 3, 4, or Lanthanide metals which are in the +2, +3, or +4 formal oxidation state. Preferred compounds include metal complexes containing from 1 to 3 π-bonded anionic or neutral ligand groups, which may be cyclic or non-cyclic delocalized π-bonded anionic ligand groups. Exemplary of such π-bonded anionic ligand groups are conjugated or nonconjugated, cyclic or non-cyclic dienyl groups, allyl groups, boratabenzene groups, and arene groups. By the term "π-bonded" is meant that the ligand group is bonded to the transition metal by a sharing or donating of electrons from a partially delocalized π-bond.

Each atom in the delocalized π-bonded group may independently be substituted with a radical selected from the group consisting of hydrogen, halogen, hydrocarbyl, halohydrocarbyl, hydrocarbyl-substituted metalloid radicals wherein the metalloid is selected from Group 14 of the Periodic Table of the Elements, and such hydrocarbyl- or hydrocarbyl-substituted metalloid radicals further substituted with a Group 15 or 16 hetero atom containing moiety. Included within the term "hydrocarbyl" are $C_{1-20}$ straight, branched and cyclic alkyl radicals, $C_{6-20}$ aromatic radicals, $C_{7-20}$ alkyl-substituted aromatic radicals, and $C_{7-20}$ aryl-substituted alkyl radicals. In addition two or more such radicals may together form a fused ring system, including partially or fully hydrogenated fused ring systems, or they may form a metallocycle with the metal. Suitable hydrocarbyl-substituted organometalloid radicals include mono-, di- and tri-substituted organometalloid radicals of Group 14 elements wherein each of the hydrocarbyl groups contains from 1 to 20 carbon atoms. Examples of suitable hydrocarbyl-substituted organometalloid radicals include trimethylsilyl, triethylsilyl, ethyldimethylsilyl, methyldiethylsilyl, triphenylgermyl, and trimethylgermyl groups. Examples of Group 15 or 16 hetero atom containing moieties include amine, phosphine, ether or thioether moieties or divalent derivatives thereof, e.g., amide, phosphide, ether or thioether groups bonded to the transition metal or Lanthanide metal, and bonded to the hydrocarbyl group or to the hydrocarbyl-substituted metalloid containing group.

Examples of suitable anionic, delocalized π-bonded groups include cyclopentadienyl, indenyl, fluorenyl, tetrahydroindenyl, tetrahydrofluorenyl, octahydrofluorenyl, pentadienyl, cyclohexadienyl, dihydroanthracenyl, hexahydroanthracenyl, decahydroanthracenyl groups, and boratabenzene groups, as well as $C_{1-10}$ hydrocarbyl-substituted or $C_{1-10}$ hydrocarbyl-substituted silyl substituted derivatives thereof. Preferred anionic delocalized π-bonded groups are cyclopentadienyl, pentamethylcyclopentadienyl, tetramethylcyclopentadienyl, tetramethylsilylcyclo-pentadienyl, indenyl, 2,3-dimethylindenyl, fluorenyl, 2-methylindenyl, 2-methyl-4-phenylindenyl, tetrahydrofluorenyl, octahydrofluorenyl, and tetrahydroindenyl.

The boratabenzenes are anionic ligands which are boron containing analogues to benzene. They are previously known in the art having been described by G. Herberich, et al., in *Organometallics*, 14,1, 471-480 (1995). Preferred boratabenzenes correspond to the formula:

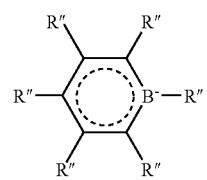

wherein R" is selected from the group consisting of hydrocarbyl, silyl, or germyl, said R" having up to 20 non-hydrogen atoms. In complexes involving divalent derivatives of such delocalized π-bonded groups one atom thereof is bonded by means of a covalent bond or a covalently bonded divalent group to another atom of the complex thereby forming a bridged system.

A suitable class of catalysts are transition metal complexes corresponding to the formula:

$$K'_kMZ'_mL_lX_p, \text{ or a dimer thereof}$$

wherein:

K' is an anionic group containing delocalized π-electrons through which K' is bound to M, said K' group containing up to 50 atoms not counting hydrogen atoms, optionally two K' groups may be joined together forming a bridged structure, and further optionally one K' may be bound to Z';

M is a metal of Group 4 of the Periodic Table of the Elements in the +2, +3 or +4 formal oxidation state;

Z' is an optional, divalent substituent of up to 50 non-hydrogen atoms that together with K forms a metallocycle with M;

L is an optional neutral ligand having up to 20 non-hydrogen atoms;

X each occurrence is a monovalent, anionic moiety having up to 40 non-hydrogen atoms, optionally, two X groups may be covalently bound together forming a divalent dianionic moiety having both valences bound to M, or, optionally 2 X groups may be covalently bound together to form a neutral, conjugated or nonconjugated diene that is bound to M by means of delocalized π-electrons (whereupon M is in the +2 oxidation state), or further optionally one or more X and one or more L groups may be bonded together thereby forming a moiety that is both covalently bound to M and coordinated thereto by means of Lewis base functionality;

k is 0, 1 or 2;

m is 0 or 1;

l is a number from 0 to 3;

p is an integer from 0 to 3; and the sum, k+m+p, is equal to the formal oxidation state of M, except when 2 X groups together form a neutral conjugated or non-conjugated diene that is bound to M via delocalized π-electrons, in which case the sum k+m is equal to the formal oxidation state of M.

Preferred complexes include those containing either one or two K' groups. The latter complexes include those containing a bridging group linking the two K' groups. Preferred bridging groups are those corresponding to the formula $(ER'_2)_x$ wherein E is silicon, germanium, tin, or carbon, R' independently each occurrence is hydrogen or a group selected from silyl, hydrocarbyl, hydrocarbyloxy and combinations thereof, said R' having up to 30 carbon or silicon atoms, and x is 1 to 8. Preferably, R' independently each occurrence is methyl, ethyl, propyl, benzyl, tert-butyl, phenyl, methoxy, ethoxy or phenoxy.

Examples of the complexes containing two K' groups are compounds corresponding to the formula:

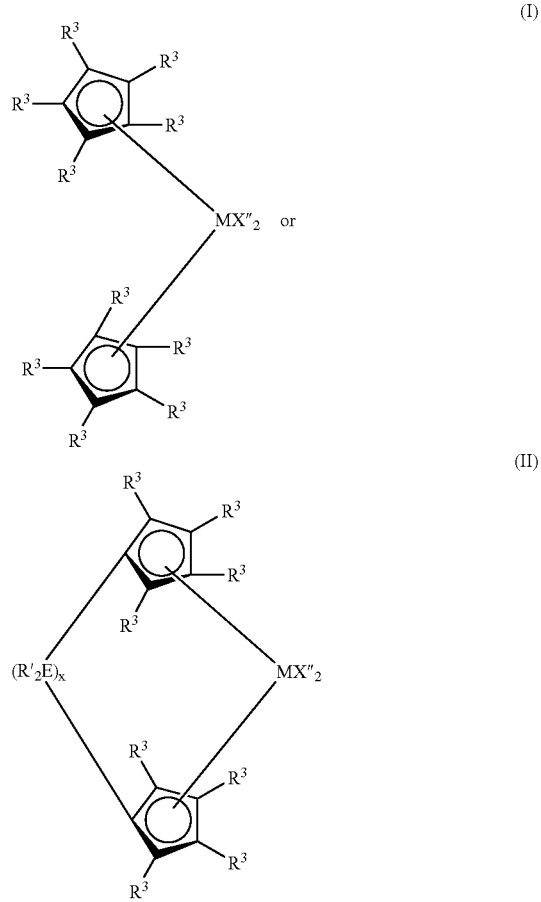

wherein:

M is titanium, zirconium or hafnium, preferably zirconium or hafnium, in the +2 or +4 formal oxidation state;

$R^3$ in each occurrence independently is selected from the group consisting of hydrogen, hydrocarbyl, silyl, germyl, cyano, halo and combinations thereof, said $R^3$ having up to 20 non-hydrogen atoms, or adjacent $R^3$ groups together form a divalent derivative (that is, a hydrocarbadiyl, siladiyl or germadiyl group) thereby forming a fused ring system, and X" independently each occurrence is an anionic ligand group of up to 40 non-hydrogen atoms, or two X" groups together form a divalent anionic ligand group of up to 40 non-hydrogen atoms or together are a conjugated diene having from 4 to 30 non-hydrogen atoms bound by means of delocalized π-electrons to M, whereupon M is in the +2 formal oxidation state, and R', E and x are as previously defined.

The foregoing metal complexes are especially suited for the preparation of polymers having stereoregular molecular structure. In such capacity it is preferred that the complex possesses $C_s$ or $C_2$ symmetry or possesses a chiral, stereorigid structure. Examples of the first type are compounds possessing different delocalized π-bonded ligand groups, such as one cyclopentadienyl group and one fluorenyl group. Similar systems based on Ti(IV) or Zr(IV) were disclosed for preparation of syndiotactic olefin polymers in Ewen, et al., *J. Am. Chem. Soc.* 110, 6255-6256 (1980). Examples of chiral structures include rac bis-indenyl complexes. Similar systems based on Ti(IV) or Zr(IV) were disclosed for preparation of isotactic olefin polymers in Wild et al., *J. Organomet. Chem.*, 232, 233-47, (1982).

Exemplary bridged ligands containing two π-bonded groups are: dimethylbis(cyclopentadienyl)silane, dimethylbis(tetramethylcyclopentadienyl)silane, dimethylbis(2-ethylcyclopentadien-1-yl)silane, dimethylbis(2-t-butylcyclopentadien-1-yl)silane, 2,2-bis(tetramethylcyclopentadienyl) propane, dimethylbis(inden-1-yl)silane, dimethylbis (tetrahydroinden-1-yl)silane, dimethylbis(fluoren-1-yl) silane, dimethylbis(tetrahydrofluoren-1-yl)silane, dimethylbis(2-methyl-4-phenylinden-1-yl)-silane, dimethylbis(2-methylinden-1-yl)silane, dimethyl(cyclopentadienyl) (fluoren-1-yl)silane, dimethyl(cyclopentadienyl)(octahydrofluoren-1-yl)silane, dimethyl(cyclopentadienyl) (tetrahydrofluoren-1-yl)silane, (1,1,2,2-tetramethy)-1,2-bis (cyclopentadienyl)disilane, (1,2-bis(cyclopentadienyl) ethane, and dimethyl(cyclopentadienyl)-1-(fluoren-1-yl) methane.

Preferred X" groups are selected from hydride, hydrocarbyl, silyl, germyl, halohydrocarbyl, halosilyl, silylhydrocarbyl and aminohydrocarbyl groups, or two X" groups together form a divalent derivative of a conjugated diene or else together they form a neutral, π-bonded, conjugated diene. Most preferred X" groups are $C_{1-20}$ hydrocarbyl groups.

A further class of metal complexes utilized in the present invention corresponds to the preceding formula $K'_k MZ'_m L_n X_p$, or a dimer thereof, wherein Z' is a divalent substituent of up to 50 non-hydrogen atoms that together with K' forms a metallocycle with M.

Preferred divalent Z' substituents include groups containing up to 30 non-hydrogen atoms comprising at least one atom that is oxygen, sulfur, boron or a member of Group 14 of the Periodic Table of the Elements directly attached to K', and a different atom, selected from the group consisting of nitrogen, phosphorus, oxygen or sulfur that is covalently bonded to M.

A preferred class of such Group 4 metal coordination complexes used according to the present invention corresponds to the formula:

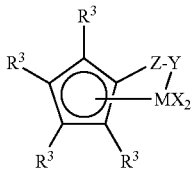

wherein:

M is titanium or zirconium, preferably titanium in the +2, +3, or +4 formal oxidation state;

$R^3$ in each occurrence independently is selected from the group consisting of hydrogen, hydrocarbyl, silyl, germyl, cyano, halo and combinations thereof, said $R^3$ having up to 20 non-hydrogen atoms, or adjacent $R^3$ groups together form a divalent derivative (that is, a hydrocarbadiyl, siladiyl or germadiyl group) thereby forming a fused ring system, each X is a halo, hydrocarbyl, hydrocarbyloxy or silyl group, said group having up to 20 non-hydrogen atoms, or two X groups together form a neutral $C_{5-30}$ conjugated diene or a divalent derivative thereof;

Y is —O—, —S—, —NR'—, —PR'—; and

Z is SiR'$_2$, CR'$_2$, SiR'$_2$SiR'$_2$, CR'$_2$CR'$_2$, CR'=CR', CR'$_2$SiR'$_2$, or GeR'$_2$, wherein R' is as previously defined.

Illustrative Group 4 metal complexes that may be employed in the practice of the present invention include:
cyclopentadienyltitaniumtrimethyl,
cyclopentadienyltitaniumtriethyl,
cyclopentadienyltitaniumtriisopropyl,
cyclopentadienyltitaniumtriphenyl,
cyclopentadienyltitaniumtribenzyl,
cyclopentadienyltitanium-2,4-dimethylpentadienyl,
cyclopentadienyltitanium-2,4-dimethylpentadienyl•triethylphosphine,
cyclopentadienyltitanium-2,4-dimethylpentadienyl•trimethylphosphine,
cyclopentadienyltitaniumdimethylmethoxide,
cyclopentadienyltitaniumdimethylchloride,
pentamethylcyclopentadienyltitaniumtrimethyl,
indenyltitaniumtrimethyl,
indenyltitaniumtriethyl,
indenyltitaniumtripropyl,
indenyltitaniumtriphenyl,
tetrahydroindenyltitaniumtribenzyl,
pentamethylcyclopentadienyltitaniumtriisopropyl,
pentamethylcyclopentadienyltitaniumtribenzyl,
pentamethylcyclopentadienyltitaniumdimethylmethoxide,
pentamethylcyclopentadienyltitaniumdimethylchloride,
bis($\eta^5$-2,4-dimethylpentadienyl) titanium,
bis($\eta^5$-2,4-dimethylpentadienyl) titanium•trimethylphosphine,
bis($\eta^5$-2,4-dimethylpentadienyl)titanium•triethylphosphine,
octahydrofluorenyltitaniumtrimethyl,
tetrahydroindenyltitaniumtrimethyl,
tetrahydrofluorenyltitaniumtrimethyl,
(tert-butylamido)(1,1-dimethyl-2,3,4,9,10-η-1,4,5,6,7,8-hexahydronaphthalenyl)dimethylsilanetitaniumdimethyl,
(tert-butylamido)(1,1,2,3-tetramethyl-2,3,4,9,10-η-1,4,5,6,7,8-hexahydronaphthalenyl)dimethylsilanetitaniumdimethyl,
(tert-butylamido)(tetramethyl-$\eta^5$-cyclopentadienyl)dimethylsilanetitanium dibenzyl,
(tert-butylamido)(tetramethyl-$\eta^5$-cyclopentadienyl)dimethylsilanetitanium dimethyl,
(tert-butylamido)(tetramethyl-$\eta^5$-cyclopentadienyl)-1,2-ethanediyltitanium dimethyl,
(tert-butylamido)(tetramethyl-$\eta^5$-indenyl)dimethylsilanetitanium dimethyl,
(tert-butylamido)(tetramethyl-5-cyclopentadienyl)dimethylsilane titanium (III) 2-(dimethylamino)benzyl;
(tert-butylamido)(tetramethyl-$\eta^5$-cyclopentadienyl)dimethylsilanetitanium (III) allyl,
(tert-butylamido)(tetramethyl-$\eta^5$-cyclopentadienyl)dimethylsilanetitanium (III) 2,4-dimethylpentadienyl,
(tert-butylamido)(tetramethyl-$\eta^5$-cyclopentadienyl)dimethylsilanetitanium (II) 1,4-diphenyl-1,3-butadiene,
(tert-butylamido)(tetramethyl-$\eta^5$-cyclopentadienyl)dimethylsilanetitanium (II) 1,3-pentadiene,
(tert-butylamido)(2-methylindenyl)dimethylsilanetitanium (II) 1,4-diphenyl-1,3-butadiene,
(tert-butylamido)(2-methylindenyl)dimethylsilanetitanium (II) 2,4-hexadiene,
(tert-butylamido)(2-methylindenyl)dimethylsilanetitanium (IV) 2,3-dimethyl-1,3-butadiene,
(tert-butylamido)(2-methylindenyl)dimethylsilanetitanium (IV) isoprene,
(tert-butylamido)(2-methylindenyl)dimethylsilanetitanium (IV) 1,3-butadiene,
(tert-butylamido)(2,3-dimethylindenyl)dimethylsilanetitanium (IV) 2,3-dimethyl-1,3-butadiene,
(tert-butylamido)(2,3-dimethylindenyl)dimethylsilanetitanium (IV) isoprene
(tert-butylamido)(2,3-dimethylindenyl)dimethylsilanetitanium (IV) dimethyl
(tert-butylamido)(2,3-dimethylindenyl)dimethylsilanetitanium (IV) dibenzyl
(tert-butylamido)(2,3-dimethylindenyl)dimethylsilanetitanium (IV) 1,3-butadiene,
(tert-butylamido)(2,3-dimethylindenyl)dimethylsilanetitanium (II) 1,3-pentadiene,
(tert-butylamido)(2,3-dimethylindenyl)dimethylsilanetitanium (II) 1,4-diphenyl-1,3-butadiene,
(tert-butylamido)(2-methylindenyl)dimethylsilanetitanium (II) 1,3-pentadiene,
(tert-butylamido)(2-methylindenyl)dimethylsilanetitanium (IV) dimethyl,
(tert-butylamido)(2-methylindenyl)dimethylsilanetitanium (IV) dibenzyl,
(tert-butylamido)(2-methyl-4-phenylindenyl)dimethylsilanetitanium (II) 1,4-diphenyl-1,3-butadiene,
(tert-butylamido)(2-methyl-4-phenylindenyl)dimethylsilanetitanium (II) 1,3-pentadiene,
(tert-butylamido)(2-methyl-4-phenylindenyl)dimethylsilanetitanium (II) 2,4-hexadiene,
(tert-butylamido)(tetramethyl-$\eta^5$-cyclopentadienyl)dimethyl-silanetitanium (IV) 1,3-butadiene,
(tert-butylamido)(tetramethyl-$\eta^5$-cyclopentadienyl)dimethylsilanetitanium (IV) 2,3-dimethyl-1,3-butadiene,
(tert-butylamido)(tetramethyl-$\eta^5$-cyclopentadienyl)dimethylsilanetitanium (IV) isoprene,
(tert-butylamido)(tetramethyl-$\eta^5$-cyclopentadienyl)dimethyl-silanetitanium (II) 1,4-dibenzyl-1,3-butadiene,
(tert-butylamido)(tetramethyl-$\eta^5$-cyclopentadienyl)dimethylsilanetitanium (II) 2,4-hexadiene,
(tert-butylamido)(tetramethyl-$\eta^5$-cyclopentadienyl)dimethyl-silanetitanium (II) 3-methyl-1,3-pentadiene, (tert-butylamido)(2,4-dimethylpentadien-3-yl)dimethylsilanetitaniumdimethyl,
(tert-butylamido) (6,6-dimethylcyclohexadienyl)dimethylsilanetitaniumdimethyl,
(tert-butylamido)(1,1-dimethyl-2,3,4,9,10-η-1,4,5,6,7,8-hexahydronaphthalen-4-yl)dimethylsilanetitaniumdimethyl,
(tert-butylamido)(1,1,2,3-tetramethyl-2,3,4,9,10-η-1,4,5,6,7,8-hexahydronaphthalen-4-yl)dimethylsilanetitaniumdimethyl
(tert-butylamido)(tetramethyl-$\eta^5$-cyclopentadienyl) methylphenylsilanetitanium (IV) dimethyl,
(tert-butylamido)(tetramethyl-$\eta^5$-cyclopentadienyl) methylphenylsilanetitanium (II) 1,4-diphenyl-1,3-butadiene,
1-(tert-butylamido)-2-(tetramethyl-$\eta^5$-cyclopentadienyl) ethanediyltitanium (IV) dimethyl, and
1-(tert-butylamido)-2-(tetramethyl-$\eta^5$-cyclopentadienyl) ethanediyl-titanium (II) 1,4-diphenyl-1,3-butadiene.

Complexes containing two K' groups including bridged complexes suitable for use in the present invention include:
bis(cyclopentadienyl)zirconiumdimethyl,
bis(cyclopentadienyl)zirconiumdibenzyl,
bis(cyclopentadienyl)zirconiummethylbenzyl,
bis(cyclopentadienyl)zirconiummethylphenyl,
bis(cyclopentadienyl)zirconiumdiphenyl,
bis(cyclopentadienyl)titanium-allyl,
bis(cyclopentadienyl)zirconiummethylmethoxide,
bis(cyclopentadienyl)zirconiummethylchloride,
bis(pentamethylcyclopentadienyl)zirconiumdimethyl,
bis(pentamethylcyclopentadienyl)titaniumdimethyl,
bis(indenyl)zirconiumdimethyl,
indenylfluorenylzirconiumdimethyl,
bis(indenyl)zirconiummethyl(2-(dimethylamino)benzyl),
bis(indenyl)zirconiummethyltrimethylsilyl,
bis(tetrahydroindenyl)zirconiummethyltrimethylsilyl,
bis(pentamethylcyclopentadienyl)zirconiummethylbenzyl,
bis(pentamethylcyclopentadienyl)zirconiumdibenzyl,
bis(pentamethylcyclopentadienyl)zirconiummethylmethoxide,
bis(pentamethylcyclopentadienyl)zirconiummethylchloride,
bis(methylethylcyclopentadienyl)zirconiumdimethyl,
bis(butylcyclopentadienyl)zirconiumdibenzyl,
bis(t-butylcyclopentadienyl)zirconiumdimethyl,
bis(ethyltetramethylcyclopentadienyl)zirconiumdimethyl,
bis(methylpropylcyclopentadienyl)zirconiumdibenzyl,
bis(trimethylsilylcyclopentadienyl)zirconiumdibenzyl,
dimethylsilyl-bis(cyclopentadienyl)zirconiumdimethyl,
dimethylsilyl-bis(tetramethylcyclopentadienyl)titanium (III) allyl
dimethylsilyl-bis(t-butylcyclopentadienyl)zirconiumdichloride,
dimethylsilyl-bis(n-butylcyclopentadienyl)zirconiumdichloride,
(methylene-bis(tetramethylcyclopentadienyl)titanium(III) 2-(dimethylamino)benzyl,
(methylene-bis(n-butylcyclopentadienyl)titanium(III) 2-(dimethylamino)benzyl,
dimethylsilyl-bis(indenyl)zirconiumbenzylchloride,
dimethylsilyl-bis(2-methylindenyl)zirconiumdimethyl,
dimethylsilyl-bis(2-methyl-4-phenylindenyl)zirconiumdimethyl,
dimethylsilyl-bis(2-methylindenyl)zirconium-1,4-diphenyl-1,3-butadiene,
dimethylsilyl-bis(2-methyl-4-phenylindenyl)zirconium (II) 1,4-diphenyl-1,3-butadiene,
dimethylsilyl-bis(tetrahydroindenyl)zirconium(II) 1,4-diphenyl-1,3-butadiene,
dimethylsilyl-bis(fluorenyl)zirconiummethylchloride,
dimethylsilyl-bis(tetrahydrofluorenyl)zirconium bis(trimethylsilyl),
(isopropylidene)(cyclopentadienyl)(fluorenyl)zirconiumdibenzyl, and
dimethylsilyl(tetramethylcyclopentadienyl)(fluorenyl)zirconium dimethyl.

Other polymerization catalysts (including Ziegler-Natta catalysts and Brookhart/Gibson catalysts) can, of course, be used in the process 120. All such catalysts (including metallocene, Ziegler-Natta and Brookhart/Gibson catalysts) are sensitive to the concentration of water in the reactor 123, i.e., the activity of such a catalyst is dependent on the concentration of water in the reactor 123. Therefore, the concentration of catalyst in the catalyst tank 132 and/or the flow rate of the catalyst solution 131 needs to be controlled depending on the concentration of water in the reactor 123.

Referring again to FIG. 8, therein is shown a chemical analysis instrument 136 calibrated using the instant invention that is the same system as shown in FIG. 4. A sample of the octane in the pipe 124 is withdrawn from the pipe 124 via a sample line 137 of 1/16 inch diameter stainless steel tubing, run through the sample injection valve of the instrument 136 and then returned to the pipe 124 via a sample return line 138 of 1/16 inch diameter stainless steel tubing. The instrument 136 is used for the on-line determination of water in the octane in the pipe 124 so that the concentration of catalyst in the catalyst tank 132 and/or the flow rate of the catalyst solution 131 flowed into the reactor 123 can be controlled.

Referring again to FIG. 1, if the liquid 11 is recycled 15, then the water concentration of the liquid 11 can be further reduced. Alternatively, several membrane dryer units can be used sequentially to further reduce the water concentration of the liquid. The water concentration of the liquid can often be reduced to less than ten parts per million with a single pass through the membrane dryer. Using the recycle technique, the water concentration of the liquid can often be reduced to less than one part per million. Ultimately, by for example using sequential membrane dryers and very dry sweep gas, the water concentration of the liquid can probably be reduced to less than one tenth of one part per million.

Figure 6:
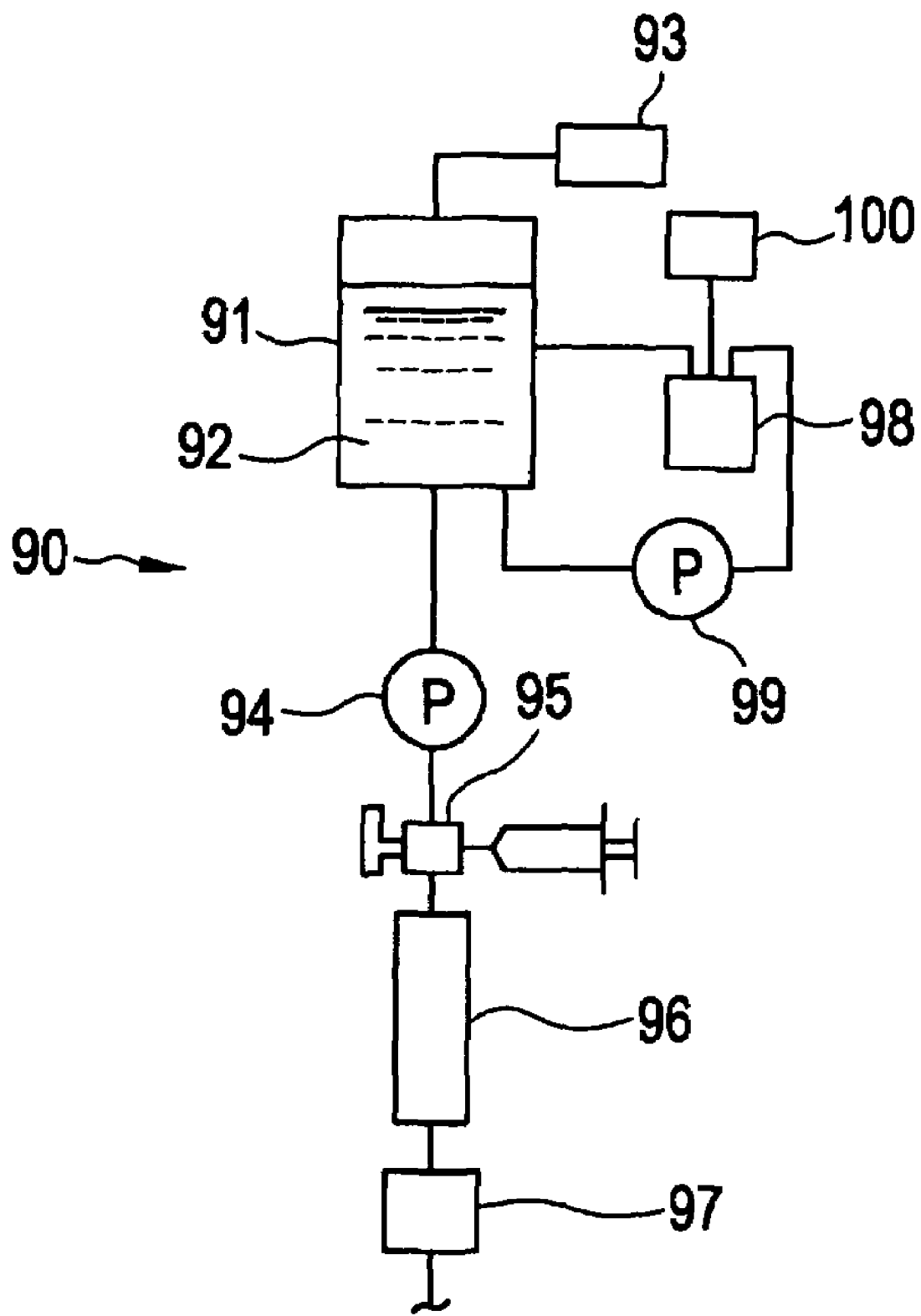
FIG. 6 is a schematic view of an improved normal phase liquid chromatography system of the instant invention.

Referring now to FIG. 6, therein is shown an improved NPLC system 90 of the instant invention that includes a reservoir 91 for containing a mobile phase 92. A vent tube 93 filled with silica gel desiccant helps to protect the mobile phase 92 from atmospheric moisture. A mobile phase pump 94 is used to pump mobile phase 92 through a sample injection valve 95, a NPLC column 96 and a detector 97. The improvement of this embodiment of the instant invention is to dry the mobile phase 92 by, for example, pumping it through a membrane dryer 98 using a pump 99. The membrane dryer 98 is preferably the same device as shown in FIG. 5 and includes a supply of dry gas 100.

Figure 7:
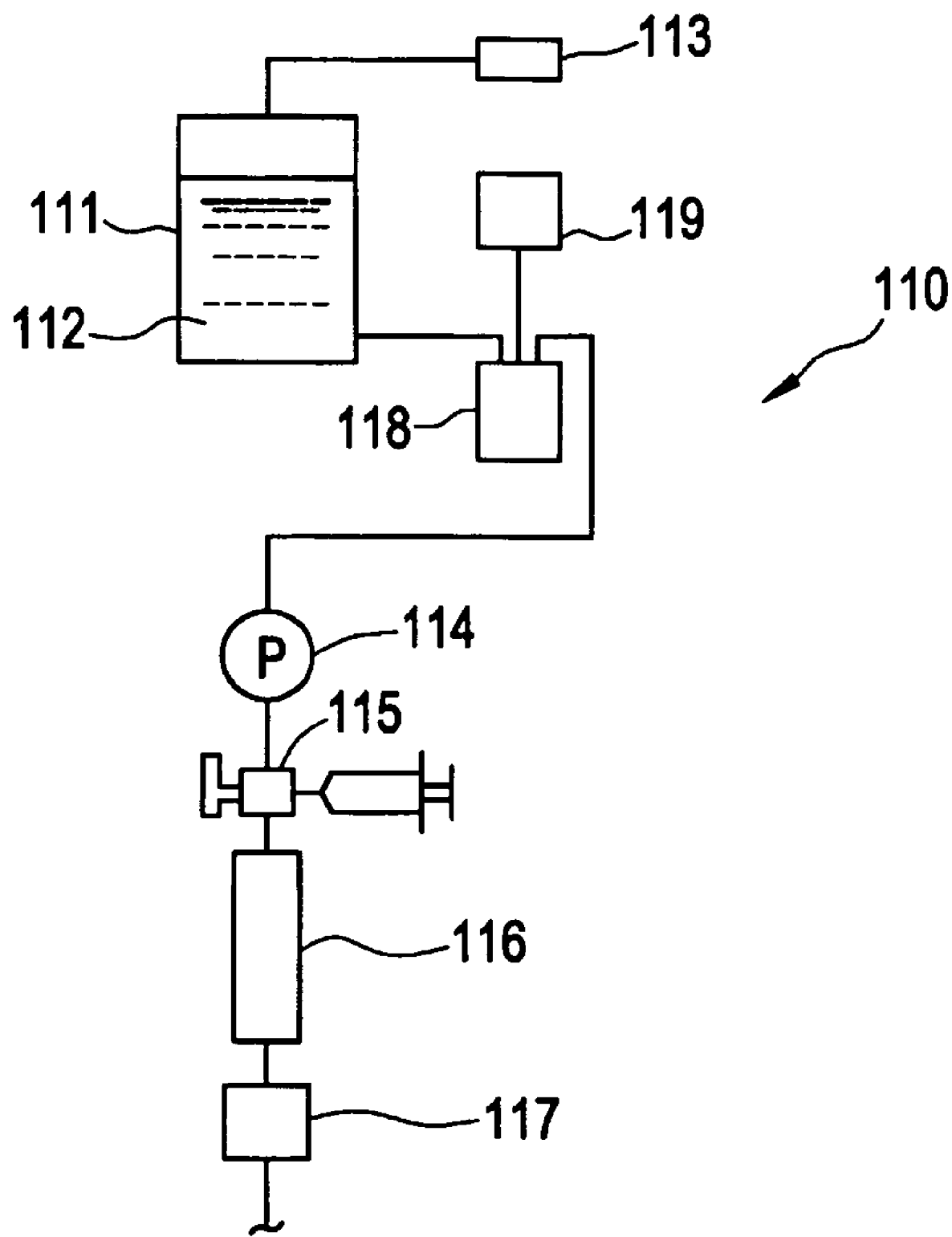
FIG. 7 is a schematic view of another improved normal phase liquid chromatography system of the instant invention.

Referring now to FIG. 7, therein is shown an improved NPLC system 110 of the instant invention that includes a reservoir 111 for containing a mobile phase 112. A vent tube 113 filled with silica gel desiccant helps to protect the mobile phase 112 from atmospheric moisture. A mobile phase pump 114 is used to pump mobile phase 112 through a membrane "dryer" 118, a sample injection valve 115, a NPLC column 116 and a detector 117. The improvement of this embodiment the instant invention is to supply the membrane dryer 118 with a source of a fluid having a controlled water concentration 119 such as a gas stream having a controlled due point. The membrane dryer 118 is preferably the same device as shown in FIG. 5.

EXAMPLE

The system shown in FIG. 3 is assembled. The liquid 33 is octane that initially contained about 78 parts per million water as determined by a coulometric Karl Fischer titration. After two hours of drying, the water concentration of the liquid 33 is 2.8 parts per million. The injection valve 36 is rotated from its load to its inject position to chromatograph the liquid 33. The response from the detector 40 for the water peak is measured by the computer 42 and allows the calibration of the system since it is known that the liquid 33 contains 2.8 parts per million water.

The system shown in FIG. 4 is assembled. The process stream 57 is a mixture of about 18% of an alkylene oxide and about 82% octane. The process stream 57 is chromatographed every thirty minutes to determine its water concentration. Over a two day period of time, the water concentration ranges from a low of 0.7 parts per million to a high of 69.7 parts per million but generally averages about 3-5 parts per million. The limit of detection for water is estimated to be about 0.1 parts per million. The linear range of analysis for water is up to about 240 parts per million.

What is claimed is:

1. A method for calibrating an analysis instrument for water analysis, comprising the steps of: (a) continuously removing water from a liquid that contains water to produce a liquid containing a reduced amount of water; (b) analyzing the liquid containing a reduced amount of water for water using a water analysis method; (c) analyzing the liquid containing a reduced amount of water using the analysis instrument to be calibrated; and (d) calibrating the analysis instrument using the analysis of step (b).

2. The method of claim 1, wherein step (a) comprises contacting the liquid that contains water with one side of a membrane that is selectively more permeable to water than the liquid in order to pass at least a portion of the water of the liquid through the membrane to produce the liquid containing a reduced amount of water.

3. The method of claim 2, wherein the water analysis method is Karl Fischer titration, wherein the membrane is comprised of a sulfonated halopolymer, wherein the liquid containing water is mixed adjacent the membrane, wherein the instrument to be calibrated is a gas chromatograph comprising a helium photoionization pulse discharge detector and wherein the water is detected by helium photoionization pulse discharge detection using the detector.

4. The method of claim 2, wherein the water analysis method is Karl Fischer titration.

5. The method of claim 4, wherein the membrane is comprised of a sulfonated halopolymer.

6. The method of claim 5, wherein the instrument to be calibrated is a gas chromatograph comprising a helium photoionization pulse discharge detector and the water is detected by helium photoionization pulse discharge detection using the detector.

7. The method of claim 2, wherein the membrane is comprised of a sulfonated halopolymer.

8. The method of claim 7, wherein the instrument to be calibrated is a gas chromatograph.

9. The method of claim 8, wherein the gas chromatograph comprises a helium photoionization pulse discharge detector and the water is detected by helium photoionization pulse discharge detection using the detector.

10. The method of claim 2, wherein the liquid containing a reduced amount of water is recycled to the one side of a membrane that is selectively more permeable to water than the liquid.

11. The method of claim 10, wherein the water analysis method is Karl Fischer titration.

12. The method of claim 10, wherein the membrane is comprised of a sulfonated halopolymer.

13. The method of claim 10, wherein the water analysis method is Karl Fischer titration and the membrane is comprised of a sulfonated halopolymer.

14. The method of claim 13, wherein the instrument to be calibrated is a gas chromatograph comprising a helium photoionization pulse discharge detector and the water is detected by helium photoionization pulse discharge detection using the detector.

15. The method of claim 10, wherein the water is analyzed by gas chromatography using a gas chromatograph comprising a helium photoionization pulse discharge detector and detected by helium photoionization pulse discharge detection using the detector.

16. The method of claim 10, wherein the liquid containing water is mixed adjacent the membrane.

17. The method of claim 16, wherein the instrument to be calibrated is a gas chromatograph comprising a helium photoionization pulse discharge detector and the water is detected by helium photoionization pulse discharge detection using the detector.

18. The method of claim 16, wherein the water analysis method is Karl Fischer titration and the membrane is comprised of a sulfonated halopolymer.

19. The method of claim 18, wherein the instrument to be calibrated is a gas chromatograph comprising a helium photoionization pulse discharge detector and the water is detected by helium photoionization pulse discharge detection using the detector.

20. The method of claim 19, wherein there is essentially no contamination by water of the liquid containing a reduced amount of water between step (a) and step (b).

21. The method of claim 2, wherein the liquid containing a reduced amount of water contains less than ten parts per million of water.

22. The method of claim 2, wherein the liquid containing a reduced amount of water contains less than one part per million of water.

23. The method of claim 2, wherein the liquid containing a reduced amount of water contains less than one tenth of one part per million of water.

24. The method of claim 2, wherein the instrument to be calibrated is a spectroscopic instrument.

25. The method of claim 24, wherein the spectroscopic instrument is selected from the group consisting of an infrared spectrometer, a near infrared spectrometer, a far infrared spectrometer, and a mass spectrometer.

26. The method of claim 25, wherein the spectroscopic instrument is a Fourier transform infrared spectrometer.

27. The method of claim 2, wherein the instrument to be calibrated is selected from the group consisting of a liquid chromatograph, and electrophoresis s instrument.

28. The method of claim 2, wherein there is essentially no contamination by water of the liquid containing a reduced amount of water between step (a) and step (b).

29. The method of claim 2, further including the step of analyzing a chemical production process fluid with the analysis instrument to determine the concentration of water in the process fluid.

30. The method of claim 29, further including the step of adding or removing water to or from the process fluid in response to the analysis of water in the process fluid.

31. The method of claim 29, wherein the chemical production process comprises the step of polymerizing one or more olefins using a polymerization catalyst.

32. The method of claim 31, wherein the amount of the polymerization catalyst used in the chemical production process is dependent on the concentration of water in the process fluid.

33. The method of claim 31, wherein the olefin is selected from the group of olefins having from two to ten carbon atoms.

34. The method of claim 33, wherein the olefin is selected from the group consisting of ethylene, propylene, norborene, octene, styrene, butadiene and divinylbenzene.

35. The method of claim 29, wherein thermal control of the chemical production process depends on controlling the water concentration of the process fluid.

36. The method of claim 1, wherein the liquid containing a reduced amount of water contains less than ten parts per million of water.

37. The method of claim 1, wherein the liquid containing a reduced amount of water contains less than one part per million of water.

38. The method of claim 1, wherein the liquid containing a reduced amount of water contains less than one tenth of one part per million of water.

39. The method of claim 1, wherein there is essentially no contamination by water of the liquid containing a reduced amount of water between step (a) and step (b).

40. The method of claim 1, further including the step of analyzing a chemical production process fluid with the analysis instrument to determine the concentration of water in the process fluid.

41. The method of claim 40, wherein the chemical production process comprises the step of polymerizing one or more olefins using a polymerization catalyst and wherein the amount of the polymerization catalyst used in the chemical production process is dependent on the concentration of water, in the process fluid.

42. An apparatus for calibrating a chemical analysis instrument for the chemical analysis of water, comprising: (a) a liquid reservoir for containing a liquid, the liquid containing water; (b) a pump in liquid communication with the liquid reservoir for pumping a liquid contained in the reservoir; (c) a membrane dryer in liquid communication with the pump for pervaporation of water from a liquid pumped through the membrane diver across a water permeable membrane into a stream of gas flowed through the membrane dryer or for diffusion of water from the stream of gas through the water permeable membrane into the liquid pumped through the membrane diver; d) a source of gas in fluid communication with the membrane diver; and (e) a chemical analysis instrument in liquid communication with the membrane diver for analyzing liquid from the membrane dryer for water, the apparatus further comprising a chemical production facility in fluid communication with the chemical analysis instrument so that the chemical analysis instrument can be used to determine the concentration of water in a process fluid of the chemical production facility.

43. The apparatus of claim 42, wherein the chemical production facility polymerizes one or more olefins using a polymerization catalyst in a chemical production process and wherein the amount of the polymerization catalyst used in the chemical production process is dependent on the concentration of water in the process fluid.

44. The apparatus of claim 42, wherein the chemical production facility polymerizes one or more olefins using a polymerization catalyst.

45. The apparatus of claim 44, wherein the olefin is selected from the group of olefins having from two to ten carbon atoms.

46. The apparatus of claim 45, wherein the olefin is selected from the group consisting of ethylene, propylene, norborene, octene, styrene, butadiene and divinylbenxene.

47. The apparatus of claim 42, wherein thermal control of the chemical production facility depends on controlling the water concentration of the process fluid.

48. A method for calibrating a chemical analysis instrument for the determination of water, comprising the steps of: (a) diffusing water from a fluid having a controlled concentration of water through a membrane into a liquid to produce a liquid containing a controlled amount of water; (b) analyzing the liquid containing a controlled amount of water for water using a water analysis method; (c) analyzing the liquid containing a controlled amount of water using the instrument to be calibrated; and (d) calibrating the analysis instrument using the analysis of step (b).

49. The method of claim 48, wherein the water analysis method is Karl Fischer titration.

50. The method of claim 48, wherein the membrane is comprised of a sulfonated halopolymer.

51. The method of claim 50, wherein the instrument to be calibrated is a gas chromatograph.

52. The method of claim 51, wherein the gas chromatograph comprises a helium photoionization pulse discharge detector and the water is detected by helium photoionization pulse discharge detection using the detector.

53. The method of claim 50, wherein the instrument to be calibrated is a spectroscopic instrument.

54. The method of claim 53, wherein the spectroscopic instrument is selected from the group consisting of an infrared spectrometer, a near infrared spectrometer, a far infrared spectrometer and a mass spectrometer.

55. The method of claim 54, wherein the spectroscopic instrument is a Fourier transform infrared spectrometer.

56. The method of claim 48, wherein the instrument to be calibrated is selected from the group consisting of a liquid chromatograph and an electrophoresis instrument.

57. The method of claim 48, further including the step of analyzing a chemical production process fluid with the analysis instrument to determine the concentration of water in the process fluid.

58. The method of claim 57, further including the step of adding or removing water to or from the process fluid in response to the analysis of water in the process fluid.

59. A method for the on-line analysis of water in a chemical production process stream, in the concentration range of from 0.01 parts per million to 100 parts per million water, comprising the steps of: (a) contacting a liquid that contains water with one side of a membrane that is selectively more permeable to water than the liquid in order to produce a liquid containing a reduced amount of water; (b) analyzing the liquid containing a reduced amount of water for water by a water analysis method; (c) analyzing the liquid containing a reduced amount of water using an analysis instrument; (d) calibrating the analysis instrument using the determination of step (b); and (e) determining the water concentration of the process stream with the analysis instrument to determine the concentration of water in the process stream.

60. The method of claim 59, wherein the liquid containing a reduced amount of water has a first water concentration and steps (a)-(c) are repeated using a liquid containing a reduced amount of water having a different water concentration than the first water concentration so that the analysis instrument is more accurately calibrated for a greater range of water concentration.

61. The method of claim 59, wherein the water concentration of the process stream is controlled using the determination of step (e).

62. The method of claim 59, wherein the water concentration of the process stream affects the activity of a catalyst used in the process.

63. The method of claim 59, wherein the water concentration of the process stream affects thermal control of the process.

* * * * *